(12) United States Patent
Britt

(10) Patent No.: US 7,178,415 B2
(45) Date of Patent: Feb. 20, 2007

(54) DUAL-OPENING SAMPLE CONTAINERS, FLUID SAMPLING DEVICE AND METHOD OF USING SAME

(76) Inventor: Sanford L. Britt, 10101 Lanark St., Sun Valley, CA (US) 91352

( * ) Notice: Subject to any disclaimer, the term of this patent is extended or adjusted under 35 U.S.C. 154(b) by 117 days.

(21) Appl. No.: 10/792,041

(22) Filed: Mar. 3, 2004

(65) Prior Publication Data

US 2004/0173035 A1 Sep. 9, 2004

Related U.S. Application Data

(60) Provisional application No. 60/451,196, filed on Mar. 3, 2003.

(51) Int. Cl.
*G01N 1/00* (2006.01)
(52) U.S. Cl. .................................. 73/864.67
(58) Field of Classification Search ............ 73/864.63, 73/864.65, 864.66, 864.67, 863.71, 864.33, 73/864.74, 864.07
See application file for complete search history.

(56) References Cited

U.S. PATENT DOCUMENTS

| | | | | |
|---|---|---|---|---|
| 1,511,223 A | * | 10/1924 | La Chapelle | 73/864.63 |
| 3,339,417 A | * | 9/1967 | Richard | 73/863.31 |
| 3,489,012 A | * | 1/1970 | Niskin | 73/863.31 |
| 3,968,696 A | * | 7/1976 | Rosenblum | 73/864.63 |
| 3,991,627 A | * | 11/1976 | Laird et al. | 73/864.16 |
| 4,037,477 A | | 7/1977 | Niskin | |
| 4,078,433 A | | 3/1978 | McCabe, Jr. et al. | |
| 4,091,676 A | | 5/1978 | Niskin | |
| 4,590,810 A | | 5/1986 | Hunkin et al. | |
| 4,625,574 A | * | 12/1986 | Robbins | 73/864.63 |
| 5,031,469 A | * | 7/1991 | Blackburn et al. | 73/864.63 |
| 5,094,113 A | | 3/1992 | Wood | |
| 5,341,692 A | * | 8/1994 | Sher et al. | 73/864.63 |
| 5,341,693 A | * | 8/1994 | Banu | 73/864.67 |
| 5,410,919 A | | 5/1995 | Carpenter et al. | |
| 5,454,275 A | | 10/1995 | Kabis | |
| 5,460,056 A | * | 10/1995 | Phillips | 73/864.66 |
| 5,487,314 A | | 1/1996 | Phillips | |
| 5,686,673 A | | 11/1997 | Kabis | |
| 5,804,743 A | | 9/1998 | Vroblesky et al. | |

(Continued)

FOREIGN PATENT DOCUMENTS

GB 2376457 A 12/2002

*Primary Examiner*—Robert Raevis
(74) *Attorney, Agent, or Firm*—David A. Belasco; Belasco Jacobs & Townsley, LLP

(57) ABSTRACT

A fluid sampling device for use with dual-opening sample containers includes attachment members holding open end seals of the sample container that are urged to a closed position by an elastic member. The elastic member is normally within the container. The sampling device is lowered into a fluid source and fluid fills the sample container. The attachment members are released remotely by a trigger, allowing the end seals to close the open ends of the container. The sampling device is withdrawn from the fluid source and the sample container is removed from the sampling device. Securing end caps are attached to the sample container to hold the end seals in place for transport and storage of the sample container. The end seal may have a membrane central portion to permit entry of a syringe needle for sampling. The securing end cap may include a septa to assist in syringe sampling.

81 Claims, 7 Drawing Sheets

U.S. PATENT DOCUMENTS 6,006,613 A * 12/1999 Dickinson et al. ....... 73/864.66
6,196,074 B1    3/2001 Varhol
6,521,444 B1 *  2/2003 Numata et al. .......... 435/262.5

* cited by examiner

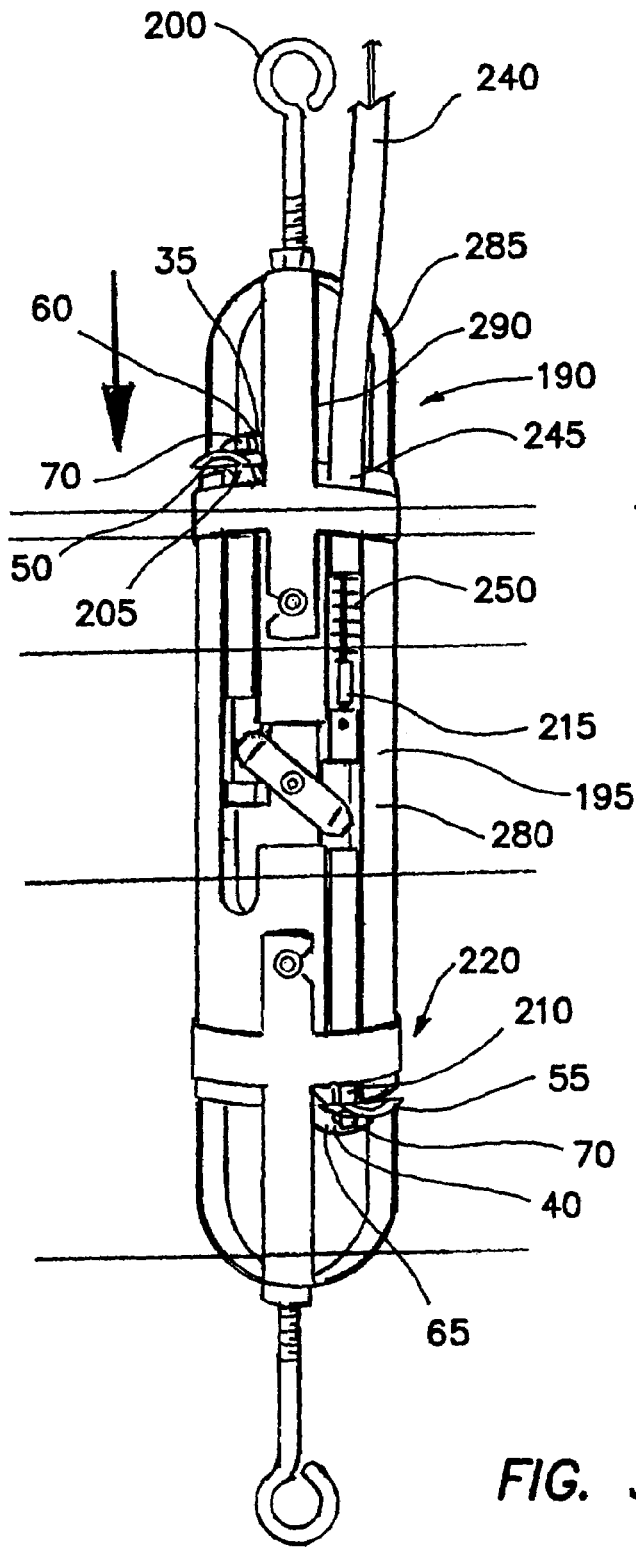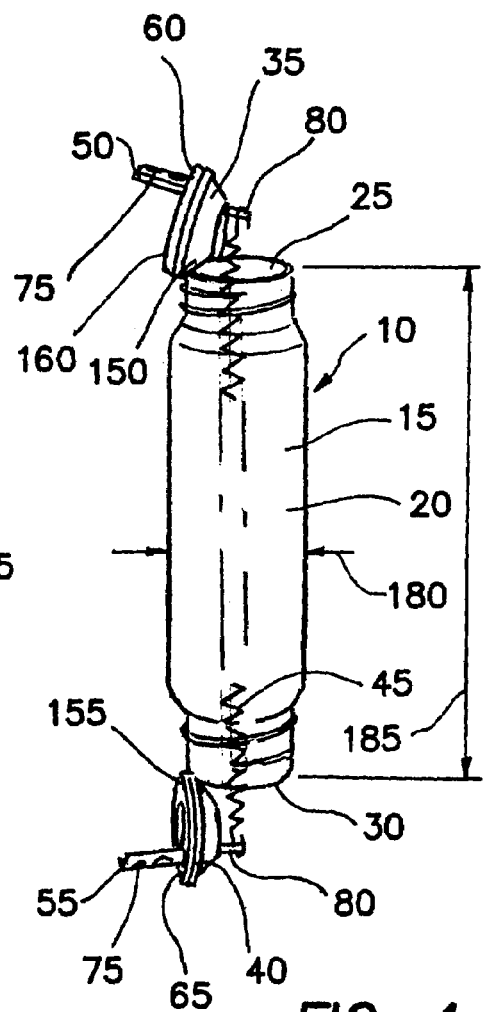
FIG. 3
FIG. 4

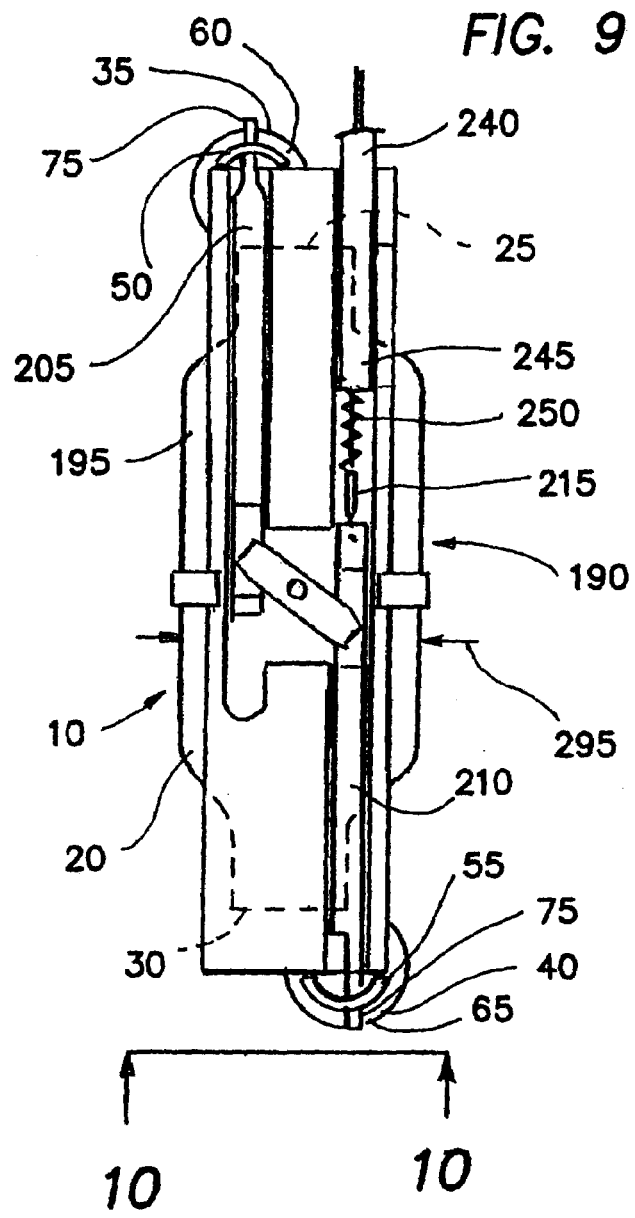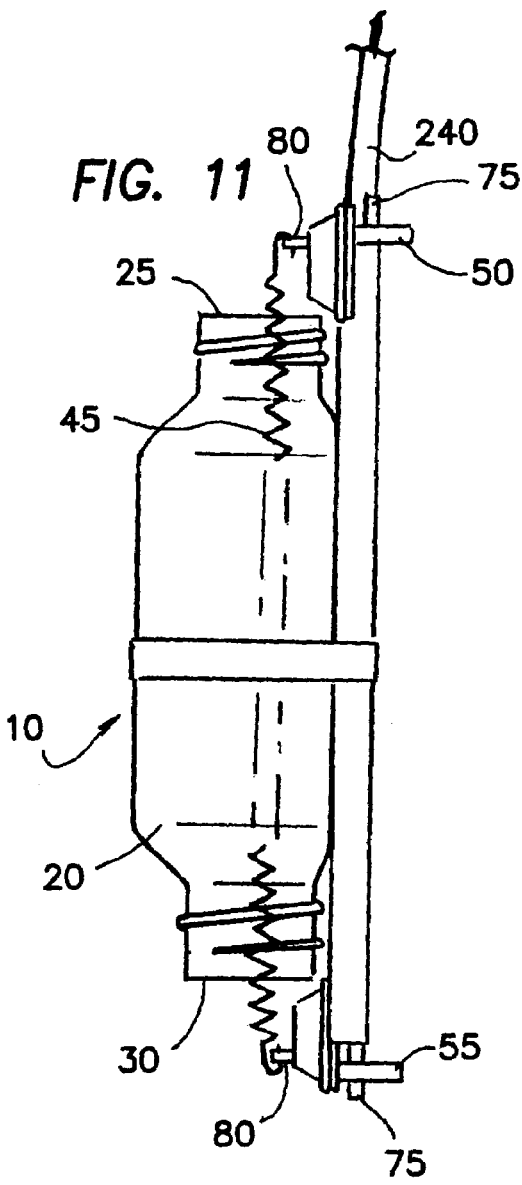

DUAL-OPENING SAMPLE CONTAINERS, FLUID SAMPLING DEVICE AND METHOD OF USING SAME

PROVISIONAL APPLICATION

Applicant claims priority of his previously filed Provisional patent application filed on Mar. 3, 2003 and having a Ser. No. of 60/451,196.

FIELD OF INVENTION

This invention pertains to fluid collection equipment for analytical testing, such as water well sample collection equipment for the environmental industry. More particularly, the invention relates to dual opening sample containers and sampling devices for use with such containers.

BACKGROUND OF THE INVENTION

Groundwater sampling in the field of environmental pollutant characterization traditionally consists of removing a specified volume of water from a groundwater well ("purging"), monitoring physical and chemical parameters of the "purged" water for indication that "fresh" ground water has been drawn into the groundwater well from the surrounding formation. This is accomplished by pumping or bailing water from the well and measuring physical and chemical parameters with instruments at the ground surface (e.g. thermometer, pH meter, electrical conductivity meter).

After purging, water samples are commonly taken from the well using a bailer and poured into containers for storage/transport to an analytical laboratory for testing. The storage and transport containers are made out of various materials such as glass or polyethylene and in sizes ranging typically from 40 milliliters to 1 liter. The size and type of container are selected based on requirements of the analysis to be performed. Volatile organic compounds such as benzene or trichloroethene are stored and transported in specifically-sized 40 milliliter volatile organic analysis (VOA vials). VOA vials are sized so that they can be placed in automated laboratory analytical equipment that use that size vial. Other analytes (e.g. metals, pesticides) are stored in different size and material containers to avoid adsorbance to the bottle material and to provide sufficient volume for analysis.

Improvements to purging/sampling techniques have been introduced by others to limit the amount, or eliminate outright, the water that needs to be "purged" from a groundwater well. These techniques include low-flow purging and no-purge "passive" methods. These methods may reduce or eliminate the need to bail water from the well after purging, but sample bottles are filled at the ground surface by pouring in the open air.

The following briefly describe traditional and newer sampling methods and equipment, and some of the disadvantages of each.

The Bailer

Fluid sampling equipment traditionally consists of some type of bailer, scoop, or pail that may or may not have a bottom filling device and some type of closure, such as a check ball or valve to contain the fluid. The sampling equipment is used to transport the fluid from the remote sampling location (inside a well or tank) to the point where the person conducting the sampling can transfer the fluid into appropriate containers for transport and/or testing. In the environmental industry, sampling from groundwater monitoring wells commonly consists of lowering a bottom-filling bailer into the well water, then raising the bailer, causing a check ball to seat—retaining the water within the bailer tube. Once the bailer is brought to the surface, the water sample is poured into containers for shipment to an analytical laboratory for testing. This method of groundwater sample collection has several disadvantages. These include:
 a) The sampled water must be poured into separate containers after the bailer is brought from the remote location to the sampling personnel.
 b) Volatile chemicals, which are commonly contaminants of concern in the groundwater to be tested, tend to off-gas when exposed to air during movement of the open sampling device and pouring into separate containers.
 c) Lowering and raising a sampling device into a groundwater well, or other fluid containing vessel, can agitate solids into suspension (induce turbidity) within the liquid to be sampled.
 d) Agitated solids, once enclosed in a bailer, are prevented from falling out of a bailer-type sampling device because of a solid bottom or check ball.
 e) Lowering a bailer through a liquid allows only limited flow through of fresh liquid, limiting the utility of sampling stratified liquids.

The Diffusion Bag Sampler

The diffusion bag sampler (U.S. Pat. Nos. 5,804,743; 6,196,074) is a no-purge, passive, sample collection device that removes some disadvantages of the bailer, but has additional disadvantages. This device consists generally of a closed polyethylene (or other material) bag with or without structural support, filled with water. In its typical use, the filled bag is lowered into a groundwater well, left for a period of time (typically two days to two weeks) while volatile organic contaminants diffuse from the surrounding water through the bag into the water contained inside the bag. The sampler is raised to the surface, and water sample is poured into separate containers for transport to an analytical laboratory. This method of groundwater sample collection has several disadvantages. These include:
 a) Like the bailer, water samples collected with the diffusion bag sampler must be poured into separate containers for transport to an analytical laboratory.
 b) Diffusion bag samplers are limited to chemicals that will diffuse through a polyethylene (or other material) membrane. Many chemicals of concern for groundwater contamination will not diffuse through polyethylene, including for example, dissolved metals; or diffuse poorly, such as methyl tertiary butyl ether (MTBE), acetone, and methyl ethyl ketone (MEK).
 c) Diffusion bag samplers must be left in place for as long as two weeks for the diffusion process to reach full equilibrium between the inside and outside of the bag.
 d) Different chemicals diffuse through the membrane at different rates, meaning that if water chemistry changes during the time the diffusion bag is deployed, it is uncertain all chemical are indeed in equilibrium inside and outside the diffusion bag.

The Niskin Bottle

The fluid sampling equipment collectively described here as the "Niskin Bottle" consists generally of an open tube with a closure device at either end that is triggered (closed) remotely (U.S. Pat. Nos. 4,037,477; 4,091,676). The sampler is ordinarily used for sea- or lake-water sampling at depth. The closure devices consist of ball valves or other closure means attached by a rubber band through the openings of the open tube. The sampler is open during deployment or opened at the designated sample point. Fluid enters the bottle at either end and is trapped within the sampler when the closures are triggered remotely. The sampler is raised to the surface, and water sample is poured into separate containers for transport to an analytical laboratory. This method of water sample collection has several disadvantages. These Include:

a) Like the bailer, water samples collected with the Niskin Bottle sampler must be poured into separate containers for transport to an analytical laboratory.

b) The Niskin Bottle in its commonly-used embodiment is large and bulky. Its size precludes it from being used in typical ground water monitoring wells used in the environmental industry (2 to 4 inch inside diameter is most common).

c) The trigger mechanism and outer appurtenances of the Niskin Bottle also do not lend themselves to insertion in groundwater monitoring wells even if they were small enough because projections from the bottle are subject to binding and catching on casing joints within monitoring wells. This could cause premature triggering of the closure mechanism or the sampler becoming stuck within the well, an obvious disadvantage for collecting a water sample from a well.

The Kabis Sampler

The Kabis Sampler (U.S. Pat. Nos. 5,454,275; 5,686,673) solves some of the problems of the bailer by utilizing a standard volatile organic analysis vial (a 40 milliliter vial) to collect samples in a monitoring well—avoiding the pouring of sample into separate sample containers. However, this method of water sample collection has several disadvantages. These Include:

a) During deployment and submergence, the Kabis sampler degasses by bubbling air through vents in the sampler. This may result in off-gassing of volatile organic compounds within the well.

b) The sample vial remains open while the sampler is brought from its remote location (in a well, for example) and until the user screws on the vial cap. This results in exposure of the water sample to the atmosphere, possibly allowing VOC off-gassing.

c) The sample vial is open only at one end. Like the bailer, solid material can become entrapped in the sample vial.

d) Deployment of the sampler also tends to agitate water in the well and can increase turbidity in collected samples.

The Kemmerer Sampler

The Kemmerer sampler (see U.S. Pat. No. 5,487,314) is similar to the Niskin Bottle in that it is comprised generally of a hollow tube with end closures that are triggered and close mechanically. A fluid sample is contained within the apparatus for retrieval from a remote source. Like the other examples described above, this sampling device has several disadvantages. These include:

a) Like the bailer, water samples collected with the Kemmerer sampler are typically poured into separate containers for transport to an analytical laboratory.

b) The Kemmerer sampler in its commonly-used embodiment is large and bulky. Its size precludes it from being used in typical ground water monitoring wells used in the environmental industry (2 to 4 inch inside diameter is typical).

c) The trigger mechanism and outer appurtenances of the Kemmerer sampler also do not lend themselves to insertion in groundwater monitoring wells even if they were small enough because projections from the bottle are subject to binding and catching on casing joints within monitoring wells. This can cause premature triggering of the closure mechanism or the sampler becoming stuck within the well, an obvious disadvantage for collecting a water sample from a well.

Other Tubular-Body Fluid Samplers

Several other examples of tubular-body samplers with various closures exist in the prior art. These other samplers are exemplified by patents such as U.S. Pat. Nos. 5,341,693; 5,094,113; 4,590,810; 4,078,433; and 5,410,919. Various closure mechanisms typically differentiate the devices.

Each of the prior art devices described above, except the Kabis sampler, require pouring of collected fluid into separate sample containers for transport and/or chemical testing at an analytical laboratory. The prior art described above includes exposure of the collected sample to the atmosphere during pouring of fluid into separate sampling containers or closure of the sample containers at the surface. This is a clear disadvantage, especially for volatile chemicals that may escape the sample and bias results.

It is an objective of the present invention to provide a means to provide a sample container that permits fluid samples to flow freely through the container to avoid well purging for groundwater sample collection and to minimize induced turbidity and solids in samples. It is a further objective to provide a sample container that may be remotely closed securely within the fluid sample so as to collect self-contain samples in a manner that precludes exposure of the sample to the atmosphere from the time of sample collection, throughout storage and transport, to the laboratory testing apparatus.

It is a still further objective of the invention to provide a fluid sampling device for remotely deploying and securing one or more sample containers. It is yet a further objective to provide securing caps for the sample container to prevent leakage and contamination during transport and storage of the sample containers so as to reliably test virtually any chemical or physical parameter in the fluid. It is still a further objective to provide a method of drawing a sample from the sample container without disturbing the container seals. It is another objective of the invention to provide a means for pressurizing the contents of the sample container without disturbing the container seals. It is yet another objective to provide a combination sample container and fluid sampling device that can fit smoothly into narrow pipes and passageways. Finally, it is an objective of the invention to provide a durable and inexpensive fluid sampling system that is adaptable to a variety of fluid sampling environments.

While some of the objectives of the present invention are disclosed in the prior art, none of the inventions found include all of the requirements identified.

SUMMARY OF THE INVENTION

The present invention addresses all of the deficiencies of fluid sampling and sample container inventions and satisfies all of the objectives described above.

(1) A dual-opening sample container can be fabricated from the following components. A body is provided. The body is formed of substantially rigid, fluid impermeable material and has a hollow cavity in communication with first and second open ends. First and second end seals are provided. The end seals are sized and shaped to fit sealably the first and second open ends. A first elastic member is provided. The first elastic member urges the first and second end seals to removably close the first and second open ends.

(2) In a variant of the invention, first and second activating protrusions are provided. Each of the activating protrusions extends outwardly from outer ends of the first and second end seals. The protrusions are sized, shaped, and located to removably engage means for holding open the end seals.

(3) In a further variant, the activating protrusion further includes holes, loops or hooks for removable engagement of the means for holding open the end seals.

(4) In still a further variant, the first and second end seals include holes, loops or hooks for attachment to the first elastic member.

(5) In another variant of the invention, the first elastic member is located within the hollow cavity.

(6) In still another variant, the first elastic member is located outside of the sample container.

(7) In a further variant, first and second securing caps are provided. The securing caps are sized and shaped to retain the first and second end seals in sealable connection with the first and second open ends of the sample container.

(8) In still a further variant, the first and second open ends of the sample container have an external thread and the first and second securing caps have a mating, internal thread.

(9) In yet a further variant, the first and second open ends of the sample container have an external bayonet mount and the first and second securing caps have a mating, internal bayonet mount.

(10) In another variant of the invention, at least one of the first and second securing caps includes a septa permitting introduction of a syringe needle and subsequent resealing of the securing cap.

(11) In yet another variant, the first and second end seals comprise a substantially rigid core. The core is surrounded by a resilient material.

(12) In a further variant, the substantially rigid core and the resilient material are coated with substantially chemically inert material.

(13) In still a further variant, the substantially chemically inert material is selected from the group that includes tetrafluoroethene, polytetrafluoroethene, perfluoralkoxy and fluoroethylpropylene.

(14) In yet another variant, the first and second end seals include a compressible seal. The seal permits an elevation of fluid pressure within the sample container upon compression of the seal.

(15) In another variant of the invention, at least one of the first and second end seals is formed of a resilient material. The resilient material permits an elevation of fluid pressure within the sample container upon compression of the seal.

(16) In still another variant, the first and second end seals have a first side. The first side is substantially conical and is sized and shaped to fit sealably into the first and second open ends of the sample container.

(17) In yet another variant, the first and second end seals have a second side. The second side has a substantially flat surface to mate with a flat inner side of either of the first and second securing caps.

(18) In a further variant of the invention, at least one of the first and second end seals has a membrane central portion. The central portion permits introduction of a syringe needle through the end seals.

(19) In still a further variant, the sample container is formed from material selected from the group that includes glass, steel and plastic.

(20) In another variant, the outside diameter of the sample container ranges from 8 mm to 60 mm.

(21) In still another variant, the overall length of the sample container ranges from 20 mm to 150 mm.

(22) In yet another variant, the sample container has a capacity ranging from 2 ml to 2400 ml.

(23) In a further variant of the invention, a fluid sampling device with dual-opening sample containers includes the following components. At least one sample container is provided. The container is formed of substantially rigid, fluid impermeable material and has a hollow cavity in communication with first and second open ends. First and second end seals are provided. The end seals are sized and shaped to fit sealably the first and second open ends. A first elastic member is provided. The first elastic member urges the first and second end seals to removably close the first and second open ends. A support platform is provided. The support platform is removably attached to the sample container and has a fixture for removable connection to a raising and lowering device. The support platform has first and second movable attachment members. The attachment members are sized, shaped and located to removably engage the first and second end seals. A trigger is provided. The trigger is located to move the attachment members from a first position to a second position. When the sample container is attached to the support platform and the first and second end seals are engaged by the first and second attachment members in the first position, the sample container will be open. The support platform may then be lowered into a fluid source by the raising and lowering device and the trigger pulled to move the first and second attachment members to the second position releasing the first and second end seals. This permits the first elastic member to urge the first and second end seals to seal the first and second open ends of the sample container. This causes a fluid sample to be sealed within the sample container. The support platform may then be withdrawn from the fluid source with the sealed sample container and the fluid sample.

(24) In a variant, a trigger sheath is provided. The sheath is sized and shaped to fit slidably over the trigger and is attached at a first end to the support platform and extends upwardly about the trigger.

(25) In another variant, a second elastic member is provided. The second elastic member urges the attachment members to the first position.

(26) In still another variant, first and second activating protrusions are provided. Each of the activating protrusions extends outwardly from outer ends of the first and second end seals and is sized, shaped, and located to removably engage the movable attachment members.

(27) In yet another variant, the activating protrusion include holes, loops or hooks for removable engagement of the movable attachment member.

(28) In a further variant, the first and second end seals include holes, loops and hooks for attachment to the first elastic member.

(29) In still a further variant, the first elastic member is disposed within the hollow cavity.

(30) In yet a further variant, the first elastic member is disposed outside of the sample container.

(31) In another variant of the invention, first and second securing caps are provided. The securing caps are sized and shaped to retain the first and second end seals in sealable connection with the first and second open ends of the sampling container.

(32) In still another variant, the first and second open ends of the sampling container have an external thread and the first and second securing caps have a mating, internal thread.

(33) In yet another variant, the first and second open ends of the sampling container have an external bayonet mount and the first and second securing caps have a mating, internal bayonet mount.

(34) In a further variant, at least one of the first and second securing caps includes a septa that permits introduction of a syringe needle and subsequent resealing of the securing cap.

(35) In still a further variant, the support platform has a hollow body. The hollow body is sized and shaped to enclose the sample container.

(36) In yet a further variant, the support platform further comprises at least one fluid-permeable protective end cover. The end cover partially encloses an open end of the hollow body.

(37) In still a further variant, the fixture for removable connection to a raising and lowering device is attached to the end cover.

(38) In another variant, the sampling container is sized and shaped to substantially enclose the support platform within outer horizontal dimensions of the sample container.

(39) In still another variant, the first and second end seals include a substantially rigid core. The core is surrounded by a resilient material.

(40) In yet another variant, the substantially rigid core and the resilient material are coated with substantially chemically inert material.

(41) In a further variant, the substantially chemically inert material is selected from the group that includes tetrafluoroethene, polytetrafluoroethene, perfluoralkoxy and fluoroethylpropylene.

(42) In still a further variant, the first and second end seals include a compressible seal. The seal permits an elevation of fluid pressure within the sample container upon compression of the seal.

(43) In yet a further variant, at least one of the first and second end seals is formed of resilient material. The resilient material permits an elevation of fluid pressure within the sample container upon compression of the seal.

(44) In still a further variant, the first and second end seals have a first side. The first side is substantially conical and is sized and shaped to fit sealably into the first and second open ends of the sample container.

(45) In another variant of the invention, the first and second end seals have a second side. The second side has a substantially flat surface to mate with a flat inner side of either the first or second securing caps.

(46) In still another variant, at least one of the first and second end seals have a membrane central portion. The central portion permits introduction of a syringe needle through the end seals.

(47) In yet another variant, the sample container is formed from material selected from the group that includes glass, steel and plastic.

(48) In a further variant, the outside diameter of the sample container ranges from 8 mm to 60 mm.

(49) In still a further variant, the overall length of the sample container ranges from 20 mm to 150 mm.

(50) In yet a further variant, the sample container has a capacity ranging from 2 ml to 2400 ml.

(51) In another variant of the invention, a method of sampling fluid using a fluid sampling device with dual-opening sample containers, includes the steps of providing at least one sample container. The container is formed of substantially rigid, fluid impermeable material and has a hollow cavity in communication with first and second open ends of the sample container. Providing first and second end seals for the container. The end seals are sized and shaped to fit sealably to the first and second open ends. Providing a first elastic member. The first elastic member urges the first and second end seals to removably close the first and second open ends. Providing a support platform.

The support platform is removably attached to the sample container and has a fixture for removable connection to a raising and lowering device. The support platform has first and second movable attachment members. The attachment members are sized, shaped and located to removably engage the first and second end seals. Providing a trigger. The trigger is located to move the attachment members from a first position to a second position. Attaching the support platform to the sample container with the movable attachment members in said first position, engaging the first and second end seals so as to maintain the end seals in an open position. Attaching the support platform to the raising and lowering device.

Lowering the support platform into a fluid source. Pulling the trigger to move the attachment members from the first position to the second position, thereby sealing the first and second open ends with a fluid sample inside of the hollow cavity. Raising the support platform from the fluid source. Removing the sealed sample container from the support platform. When the sample container is removed from the support platform, it may be sent for testing and examination without contamination from elements outside the fluid source.

(52) In yet another variant, the method of sampling fluid using a fluid sampling device with dual-opening sample containers includes the additional steps of providing first and second securing caps. The securing caps are sized and shaped to retain the first and second end seals in sealable connection with the first and second open ends of the sampling container. Attaching the first and second securing caps to the first and second open ends of the of the sample container.

(53) In a final variant, the method of sampling fluid using a fluid sampling device with dual-opening sample containers includes the additional steps of providing at least one of the first and second end seals with a membrane central portion. The central portion permits introduction of a syringe needle through the end seal. Providing first and second securing caps. The securing caps are sized and shaped to retain the first and second end seals in sealable connection with the first and second open ends of the sampling container. At least one of the securing caps has a septa to permit introduction of a syringe needle and subsequent resealing of the securing cap. Inserting a syringe needle through the septa and the membrane central portion. Withdrawing a fluid sample from the sample container. Removing the syringe needle from the septa and the membrane central portion. Depositing the fluid sample in a test facility.

An appreciation of the other aims and objectives of the present invention and an understanding of it may be achieved by referring to the accompanying drawings and the detailed description of a preferred embodiment.

DESCRIPTION OF THE DRAWINGS

FIG. 3 is a side elevational view of a first embodiment of a fluid sampling device enclosing the sample container, illustrating attachment members holding the end seals in a first, open position;

FIG. 4 is a perspective view of the FIG. 1 embodiment, illustrating the end seals in an open position;

FIG. 9 is a rear elevational view of a third embodiment of a fluid sampling device that fits within the outer diameter of the sample container;

FIG. 10 is a bottom side plan view of the FIG. 9 embodiment, from the point of view 10—10, illustrating the placement of the fluid sampling device within the outer diameter of the sample container;

FIG. 11 is a side elevational view of the FIG. 9 embodiment; and

DETAILED DESCRIPTION OF THE PREFERRED EMBODIMENT

Figure 1:
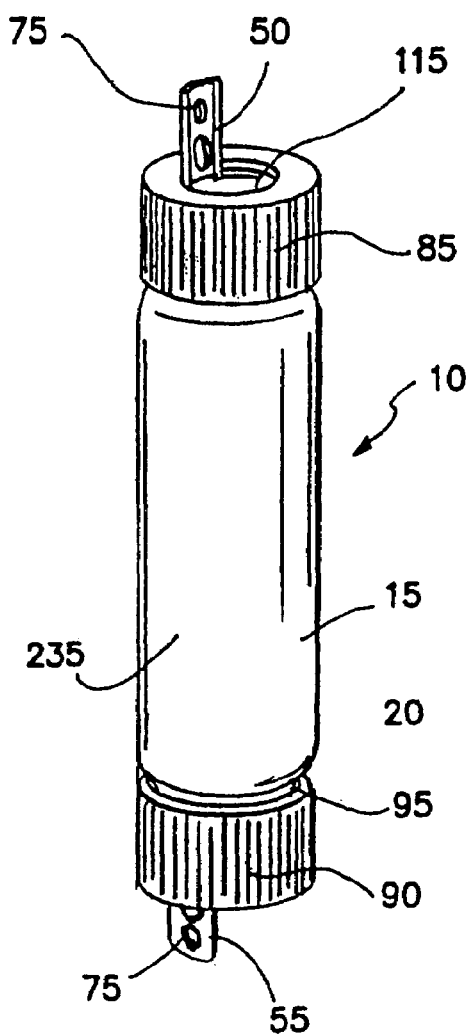
FIG. 1 is a perspective view of a dual opening sample container according to the present invention, illustrating attached securing caps.

FIGS. 1, 2, 4, 6 and 8 illustrate a dual-opening sample container 10 that can be fabricated from the following components. A body 15 is provided. The body 15 is formed of substantially rigid, fluid impermeable material and has a hollow cavity 20 in communication with first 25 and second 30 open ends. First 35 and second 40 end seals are provided. The end seals 35, 40 are sized and shaped to fit sealably the first 25 and second 30 open ends. A first elastic member 45 is provided. The first elastic member 45 urges the first 35 and second 40 end seals to removably close the first 25 and second 30 open ends.

(2) In a variant of the invention, as illustrated in FIGS. 3 and 4, first 50 and second 55 activating protrusions are provided. Each of the activating protrusions 50, 55 extends outwardly from outer ends 60, 65 of the first 35 and second 40 end seals. The protrusions 50, 55 are sized, shaped, and located to removably engage means 70 for holding open the end seals 35, 40.

(3) In a further variant, as illustrated in FIGS. 1, 2, 4, 5 and 8, the activating protrusion 50, 55 further includes holes 75, loops 77 or hooks 79 for removable engagement of the means 70 for holding open the end seals 35, 40.

(4) In still a further variant, the first 35 and second 40 end seals include holes 80, loops 77 or hooks 79 for attachment to the first elastic member 45.

(5) In another variant of the invention, the first elastic member 45 is located within the hollow cavity 20.

Figure 12:
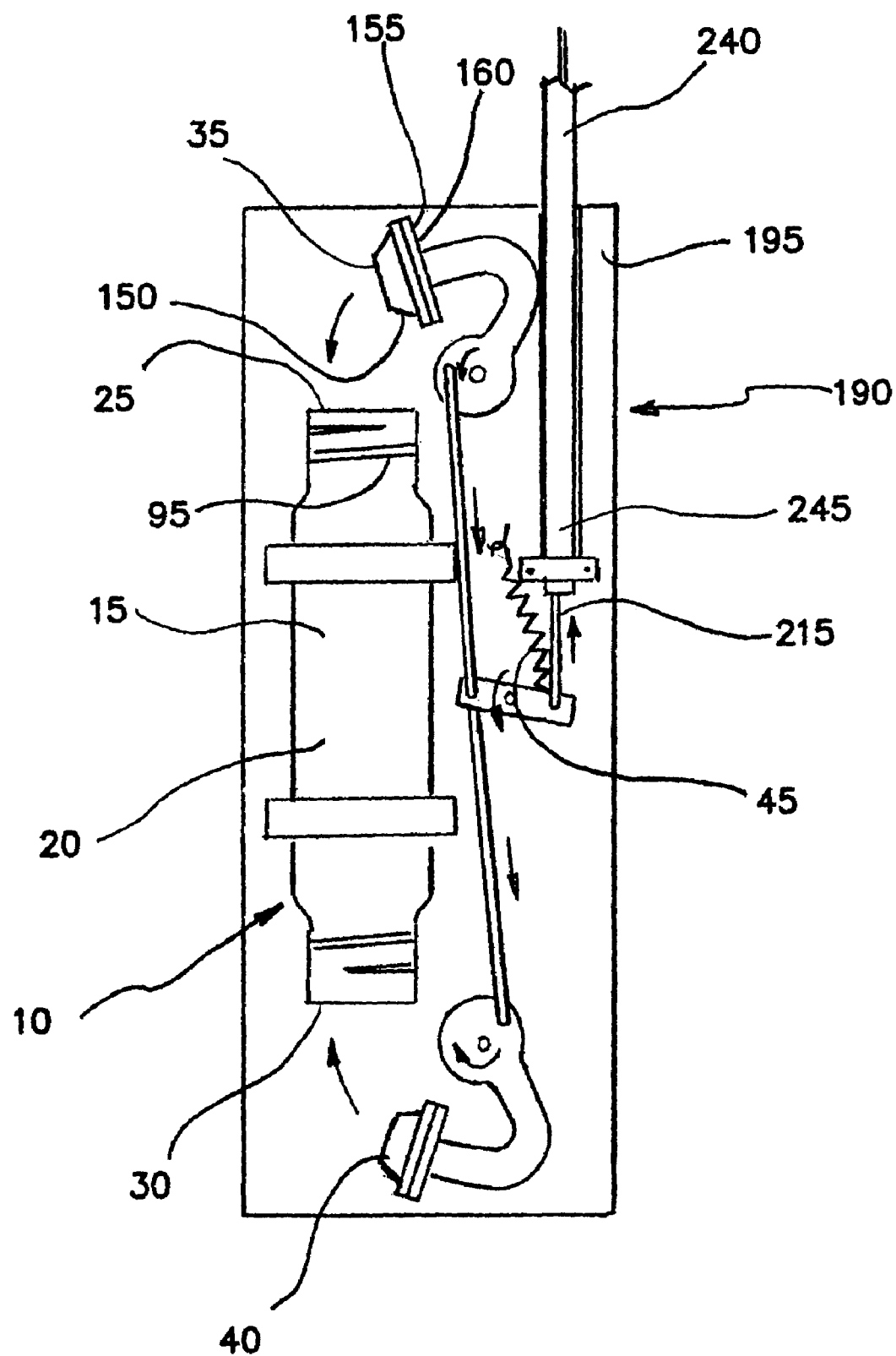
FIG. 12 is a side elevational view of a fourth embodiment of a fluid sampling device illustrating a sample container having an external elastic member.

(6) In still another variant, as illustrated in FIG. 12, the first elastic member 45 is located outside of the sample container 10.

Figure 2A:
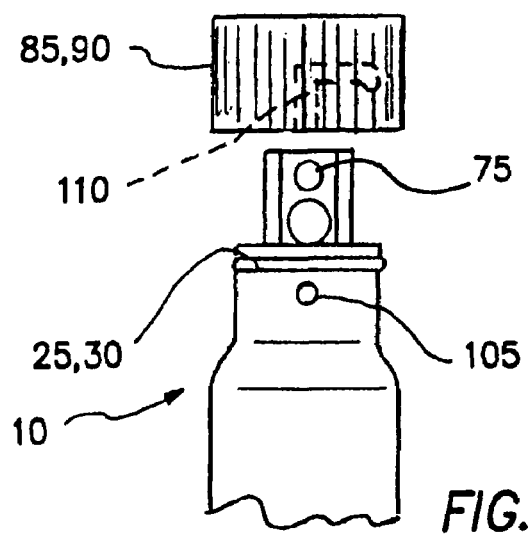
FIG. 2A is a side elevational view of the FIG. 1 embodiment, illustrating a bayonet mount securing cap.
Figure 2:
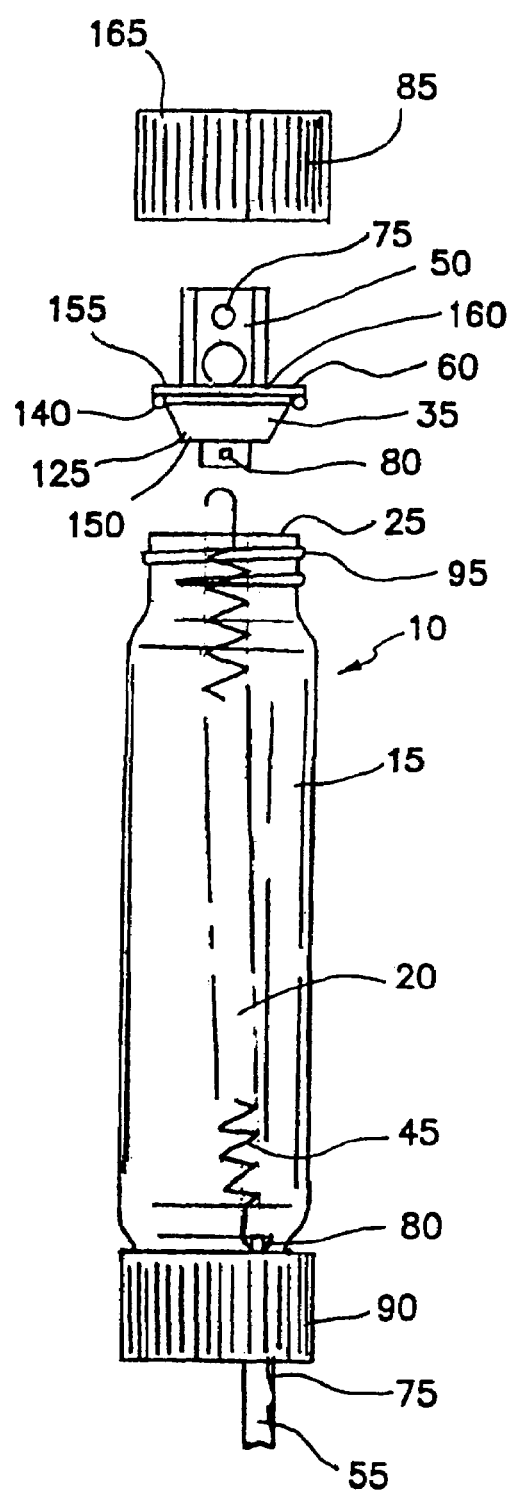
FIG. 2 is an exploded, side elevational view of the FIG. 1 embodiment, illustrating an end seal, an elastic member and securing caps with internal thread.
Figure 2B:
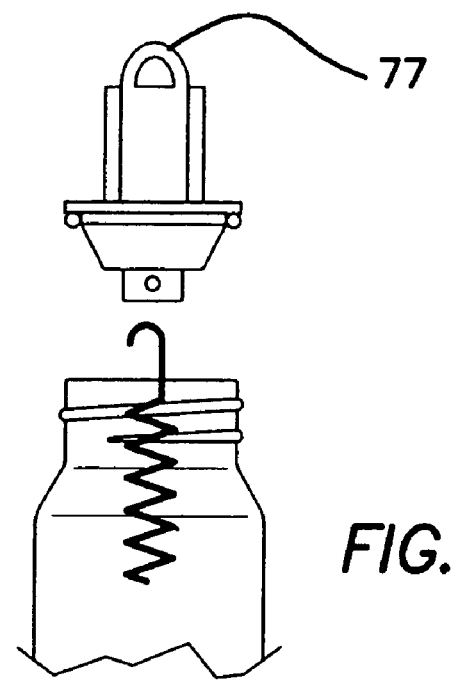
FIG. 2B is a side elevational view of the FIG. 1 embodiment, illustrating an activating protrusion comprising a loop.
Figure 2C:
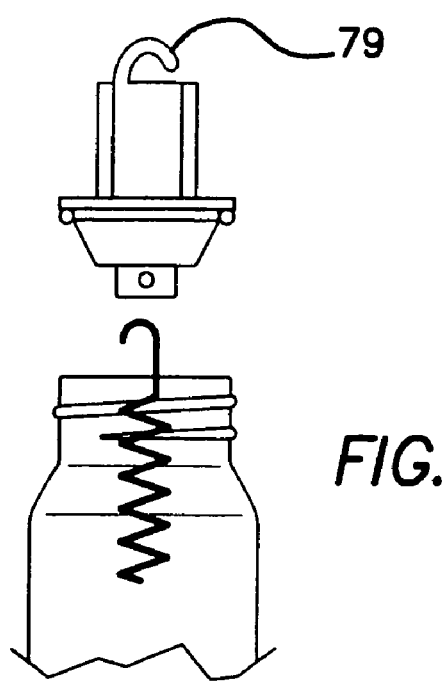
FIG. 2C is a side elevational view of the FIG. 1 embodiment, illustrating an activating protrusion comprising a hook.

(7) In a further variant, as illustrated in FIGS. 1 and 2, first 85 and second 90 securing caps are provided. The securing caps 85, 90 are sized and shaped to retain the first 35 and second 40 end seals in sealable connection with the first 25 and second 30 open ends of the sample container 10.

(8) In still a further variant, as illustrated in FIG. 2, the first 25 and second 30 open ends of the sample container 10 have an external thread 95 and the first 85 and second 90 securing caps have a mating, internal thread (not shown).

(9) In yet a further variant, as illustrated in FIG. 2A, the first 25 and second 30 open ends of the sample container 10 have an external bayonet mount 105 and the first 85 and second 90 securing caps have a mating, internal bayonet mount 110.

(10) In another variant of the invention, as illustrated in FIG. 1, at least one of the first 85 and second 90 securing caps includes a septa 115 permitting introduction of a syringe needle (not shown) and subsequent resealing of the securing cap 85, 90.

(11) In yet another variant, as illustrated in FIG. 2, the first 35 and second 40 end seals comprise a substantially rigid core 125. The core 125 is surrounded by a resilient material (not shown).

(12) In a further variant, the substantially rigid core 125 and the resilient material are coated with substantially chemically inert material (not shown).

(13) In still a further variant, the substantially chemically inert material is selected from the group that includes tetrafluoroethene, polytetrafluoroethene, perfluoralkoxy and fluoroethylpropylene.

(14) In yet a further variant, as illustrated in FIG. 2, the first 35 and second 40 end seals include a compressible seal 140. The seal 140 permits an elevation of fluid pressure within the sample container 10 upon compression of the seal 140.

(15) In another variant of the invention, at least one of the first 35 and second 40 end seals is formed of a resilient material (not shown). The resilient material permits an elevation of fluid pressure within the sample container 10 upon compression of the seal 35, 40.

(16) In still another variant, as illustrated in FIGS. 2, 4, 8, 11 and 12, the first 35 and second 40 end seals have a first side 150. The first side 150 is substantially conical and is sized and shaped to fit sealably into the first 25 and second 30 open ends of the sample container 10.

(17) In yet another variant, as illustrated in FIG. 2, the first 35 and second 40 end seals have a second side 155. The second side 155 has a substantially flat surface 160 to mate with a flat inner side 165 of either of the first 85 and second 90 securing caps.

Figures 5, 6:
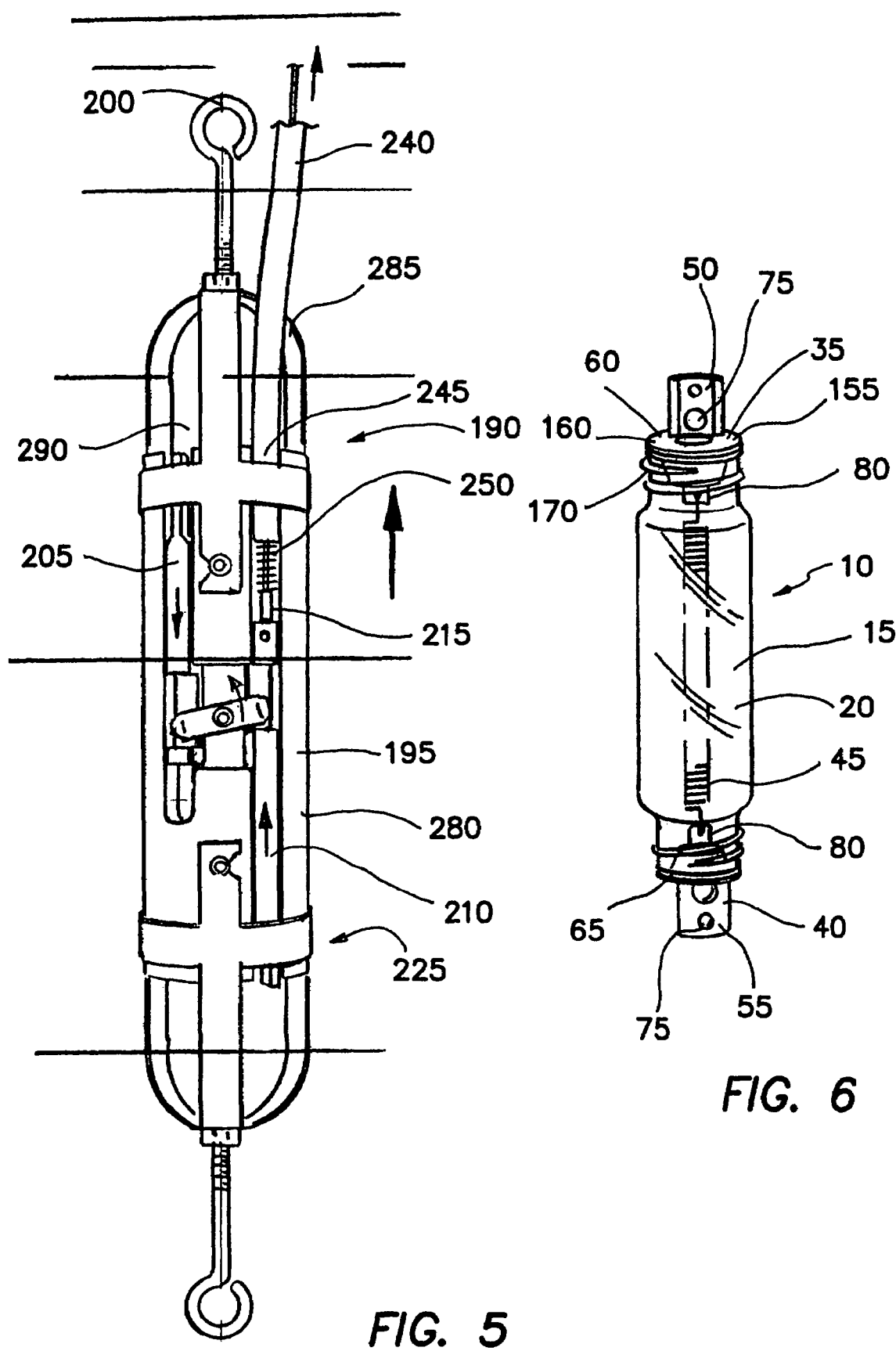
FIG. 5 is a side elevational view of the FIG. 3 embodiment, illustrating attachment members having released the end seals to a second, closed position.
FIG. 6 is a perspective view of the FIG. 1 embodiment, illustrating the end seals in a closed position.
Figure 7:
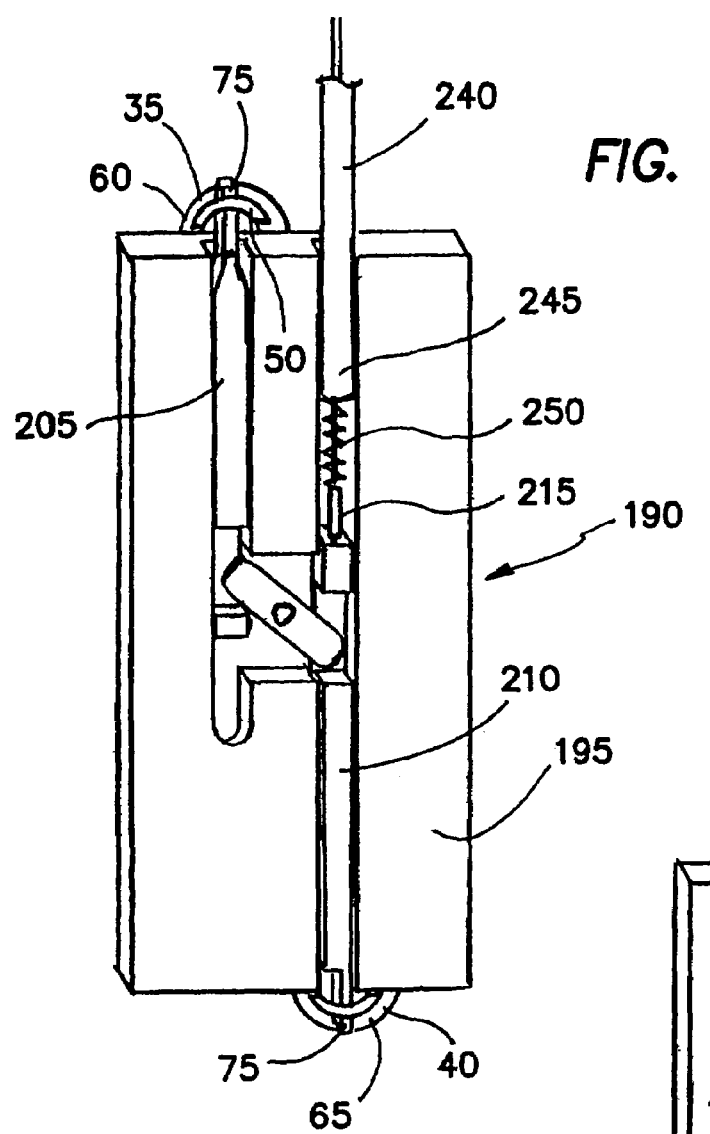
FIG. 7 is a perspective view of a back side of a second embodiment of a fluid sampling device supporting the sample container, illustrating attachment members holding the end seals in a first, open position.
Figure 8:
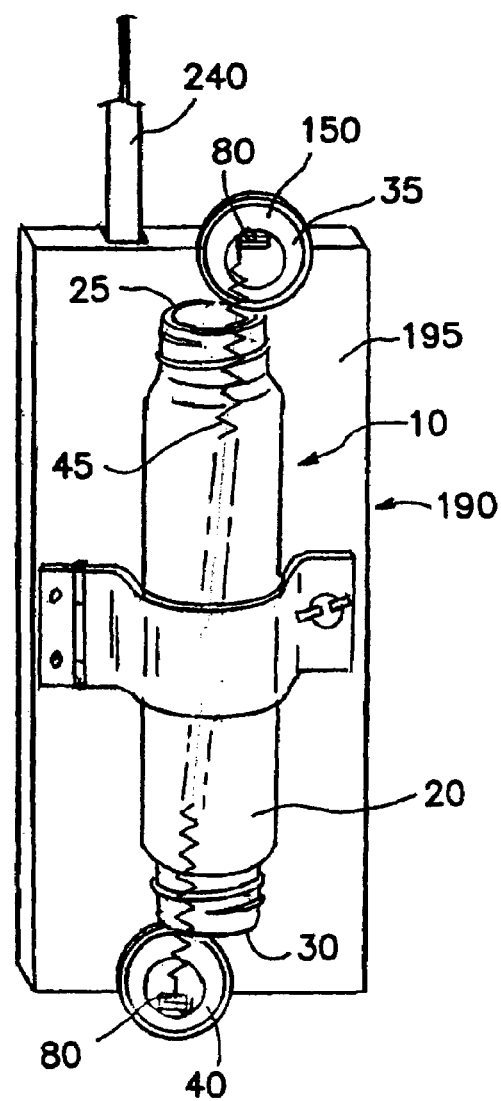
FIG. 8 is a perspective view of a front side of the FIG. 7 embodiment, illustrating attachment of the sample container.

(18) In a further variant of the invention, as illustrated in FIG. 6, at least one of the first 35 and second 40 end seals has a membrane central portion 170. The central portion 170 permits introduction of a syringe needle through the end seals 35, 40.

(19) In still a further variant, the sample container 10 is formed from material selected from the group that includes glass, steel and plastic.

(20) In another variant, as illustrated in FIG. 4, the outside diameter 180 of the sample container 10 ranges from 8 mm to 60 mm.

(21) In still another variant, as illustrated in FIG. 4, the overall length 185 of the sample container 10 ranges from 20 mm to 150 mm.

(22) In yet another variant, the sample container 10 has a capacity ranging from 2 ml to 2400 ml.

(23) In a further variant of the invention, as illustrated in FIGS. 3, 5 and 7–12, a fluid sampling device 190 with dual-opening sample containers 10 includes the following components. At least one sample container 10 is provided. The container 10 is formed of substantially rigid, fluid impermeable material and has a hollow cavity 20 in communication with first 25 and second 30 open ends. First 35 and second 40 end seals are provided. The end seals 35, 40 are sized and shaped to fit sealably the first 25 and second 30 open ends. A first elastic member 45 is provided. The first elastic member 45 urges the first 35 and second 40 end seals to removably close the first 25 and second 30 open ends. A support platform 195 is provided. The support platform 195 is removably attached to the sample container 10 and has a fixture 200 for removable connection to a raising and lowering device (not shown). The support platform 195 has first 205 and second 210 movable attachment members. The attachment members 205, 210 are sized, shaped and located to removably engage the first 35 and second 40 end seals.

A trigger 215 is provided. The trigger 215 is located to move the attachment members 205, 210 from a first position 220 to a second position 225. When the sample container 10 is attached to the support platform 195 and the first 35 and second 40 end seals are engaged by the first 205 and second 210 attachment members in the first position 220, the sample container 10 will be open. The support platform 195 may then be lowered into a fluid source (not shown) by the raising and lowering device and the trigger 215 pulled to move the first 205 and second 210 attachment members to the second position 225 releasing the first 35 and second 40 end seals. This permits the first elastic member 45 to urge the first 35 and second 40 end seals to seal the first 25 and second 30 open ends of the sample container 10. This causes a fluid sample 235 to be sealed within the sample container 10, as illustrated in FIG. 1. The support platform 195 may then be withdrawn from the fluid source with the sealed sample container 10 and the fluid sample 235.

(24) In a variant, as illustrated in FIGS. 3, 5 and 7–12, a trigger sheath 240 is provided. The sheath 240 is sized and shaped to fit slidably over the trigger 215 and is attached at a first end 245 to the support platform 195 and extends upwardly about the trigger 195.

(25) In another variant, as illustrated in FIGS. 3, 5 and 7–11, a second elastic member 250 is provided. The second elastic member 250 urges the attachment members 205, 210 to the first position 220.

(26) In still another variant, first 50 and second 55 activating protrusions are provided. Each of the activating protrusions 50, 55 extends outwardly from outer ends 60, 65 of the first 35 and second 40 end seals and is sized, shaped, and located to removably engage the movable attachment members 205, 210.

(27) In yet another variant, the activating protrusion 205, 210 include holes 75, loops 77 or hooks 79 for removable engagement of the movable attachment member 205, 210.

(28) In a further variant, the first 35 and second 40 end seals include holes 80, loops 77 and hooks 79 for attachment to the first elastic member 45.

(29) In still a further variant, the first elastic member 45 is disposed within the hollow cavity 20.

(30) In yet a further variant, as illustrated in FIG. 12, the first elastic member 45 is disposed outside of the sample container 10.

(31) In another variant of the invention, as illustrated in FIGS. 1 and 2, first 85 and second 90 securing caps are provided. The securing caps 85, 90 are sized and shaped to retain the first 35 and second 40 end seals in sealable connection with the first 25 and second 30 open ends of the sampling container 10.

(32) In still another variant, as illustrated in FIGS. 2 and 6, the first 25 and second 30 open ends of the sampling container 10 have an external thread 250 and the first 85 and second 90 securing caps have a mating, internal thread 255.

(33) In yet another variant, as illustrated in FIG. 2A, the first 25 and second 30 open ends of the sampling container 10 have an external bayonet mount 260 and the first 85 and second 90 securing caps have a mating, internal bayonet mount 265.

(34) In a further variant, as illustrated in FIG. 1, at least one of the first 85 and second 90 securing caps includes a septa 115 that permits introduction of a syringe needle 120 and subsequent resealing of the securing cap 85, 90.

(35) In still a further variant, as illustrated in FIGS. 3 and 5, the support platform 195 has a hollow body 280. The hollow body 280 is sized and shaped to enclose the sample container 10.

(36) In yet a further variant, the support platform 195 further comprises at least one fluid-permeable protective end cover 285. The end cover 285 partially encloses an open end 290 of the hollow body 280.

(37) In still a further variant, the fixture 200 for removable connection to a raising and lowering device is attached to the end cover 285.

(38) In another variant, as illustrated in FIGS. 9–11, the sampling container 10 is sized and shaped to substantially enclose the support platform 195 within outer horizontal dimensions 295 of the sample container 10.

(39) In still another variant, as illustrated in FIG. 2, the first 35 and second 40 end seals include a substantially rigid core 125. The core 125 is surrounded by a resilient material.

(40) In yet another variant, the substantially rigid core 125 and the resilient material are coated with substantially chemically inert material.

(41) In a further variant, the substantially chemically inert material is selected from the group that includes tetrafluoroethene, polytetrafluoroethene, perfluoralkoxy and fluoroethylpropylene.

(42) In still a further variant, as illustrated in FIGS. 2, 4, 8, 11 and 12, the first 35 and second 40 end seals include a compressible seal 140. The seal 140 permits an elevation of fluid pressure within the sample container 10 upon compression of the seal 140.

(43) In yet a further variant, at least one of the first 35 and second 40 end seals is formed of resilient material. The resilient material permits an elevation of fluid pressure within the sample container 10 upon compression of the seal 35, 40.

(44) In still a further variant, as illustrated in FIGS. 2, 4, 8 and 11, the first 35 and second 40 end seals have a first side 150. The first side 150 is substantially conical and is sized and shaped to fit sealably into the first 25 and second 30 open ends of the sample container 10.

(45) In another variant of the invention, as illustrated in FIG. 2, the first 35 and second 40 end seals have a second side 155. The second side 155 has a substantially flat surface 160 to mate with a flat inner side 165 of either the first 85 or second 90 securing caps.

(46) In still another variant, as illustrated in FIG. 6, at least one of the first 35 and second 40 end seals have a membrane central portion 170. The central portion 170 permits introduction of a syringe needle through the end seals 35, 40.

(47) In yet another variant, the sample container 10 is formed from material selected from the group that includes glass, steel and plastic.

(48) In a further variant, as illustrated in FIG. 4, the outside diameter 180 of the sample container 10 ranges from 8 mm to 60 mm.

(49) In still a further variant, as illustrated in FIG. 4, the overall length 185 of the sample container 10 ranges from 20 mm to 150 mm.

(50) In yet a further variant, the sample container 10 has a capacity ranging from 2 ml to 2400 ml.

(51) In another variant of the invention, a method of sampling fluid using a fluid sampling device 190 with dual-opening sample containers 10, includes the steps of providing at least one sample container 10. The container 10 is formed of substantially rigid, fluid impermeable material and has a hollow cavity 20 in communication with first 25 and second 30 open ends of the sample container 10. Providing first 35 and second 40 end seals for the container 10. The end seals 35, 40 are sized and shaped to fit sealably to the first 25 and second 30 open ends. Providing a first elastic member 45. The first elastic member 45 urges the first 35 and second 40 end seals to removably close the first 25 and second 30 open ends.

Providing a support platform 195. The support platform 195 is removably attached to the sample container 10 and has a fixture 200 for removable connection to a raising and lowering device. The support platform 195 has first 205 and second 210 movable attachment members. The attachment members 205, 210 are sized, shaped and located to removably engage the first 35 and second 40 end seals. Providing a trigger 215. The trigger 215 is located to move the attachment members 205, 210 from a first position 220 to a second position 225. Attaching the support platform 195 to the sample container 10 with the movable attachment members 205, 210 in said first position 220, engaging the first 35 and second 40 end seals so as to maintain the end seals 35, 40 in an open position 240. Attaching the support platform 195 to the raising and lowering device 175. Lowering the support platform 195 into a fluid source. Pulling the trigger 215 to move the attachment members 205, 210 from the first position 220 to the second position 225, thereby sealing the first 25 and second 30 open ends with a fluid sample 235 inside of the hollow cavity 20. Raising the support platform 195 from the fluid source. Removing the sealed sample container 10 from the support platform 195.

When the sample container 10 is removed from the support platform 195, it may be sent for testing and examination without contamination from elements (not shown) outside the fluid source.

(52) In yet another variant, the method of sampling fluid using a fluid sampling device 190 with dual-opening sample containers 10 includes the additional steps of providing first 85 and second 90 securing caps. The securing caps 85, 90 are sized and shaped to retain the first 35 and second 40 end seals in sealable connection with the first 25 and second 30 open ends of the sampling container 10. Attaching the first 85 and second 90 securing caps to the first 25 and second 30 open ends of the of the sample container 10.

(53) In a final variant, the method of sampling fluid using a fluid sampling device 190 with dual-opening sample containers 10 includes the additional steps of providing at least one of the first 35 and second 40 end seals with a membrane central portion 170. The central portion 170 permits introduction of a syringe needle 120 through the end seal 35, 40. Providing first 85 and second 90 securing caps. The securing caps 85, 90 are sized and shaped to retain the first 35 and second 40 end seals in sealable connection with the first 25 and second 30 open ends of the sampling container 10. At least one of the securing caps 85, 90 has a septa 115 to permit introduction of a syringe needle and subsequent resealing of the securing cap 85, 90. Inserting a syringe needle 120 through the septa 115 and the membrane central portion 170. Withdrawing a fluid sample 235 from the sample container 10. Removing the syringe needle from the septa 115 and the membrane central portion 170. Depositing the fluid sample 235 in a test facility.

The fluid sampling device with dual-opening sample containers 190 and dual-opening sample container 10 have been described with reference to particular embodiments. Other modifications and enhancements can be made without departing from the spirit and scope of the claims that follow.

The invention claimed is:

1. A dual-opening sample container, comprising:
a body, said body being formed of substantially rigid, fluid impermeable material and having a hollow cavity in communication with first and second open ends;
first and second end seals, said end seals being sized and shaped to fit sealably said first and second open ends;
a first elastic member, said first elastic member urging said first and second end seals to removably close said first and second open ends;
first and second activating protrusions, each of said activating protrusions extending outwardly from outer ends of said first and second end seals and being sized, shaped, and disposed to removably engage means for holding open said end seals; and
first and second removable securing caps, said securing caps permitting passage of said activating protrusions through said securing caps and being sized and shaped to retain said first and second end seals in sealable connection with said first and second open ends of said sample container.

2. The dual-opening sample container, as described in claim 1, wherein said activating protrusion further comprises any of holes, loops and hooks for removable engagement of said means for holding open said end seals.

3. The dual-opening sample container, as described in claim 1, wherein said first and second end seals further comprise any of holes, loops and hooks for attachment to said first elastic member.

4. The dual-opening sample container, as described in claim 1, wherein said first elastic member is disposed within said hollow cavity.

5. The dual-opening sample container, as described in claim 1, wherein said first elastic member is disposed outside of said sample container.

6. The dual-opening sample container, as described in claim 1, wherein said first and second open ends of said sample container have an external thread and said first and second securing caps have a mating, internal thread.

7. The dual-opening sample container, as described in claim 1, wherein said first and second open ends of said sample container have an external bayonet mount and said first and second securing caps have a mating, internal bayonet mount.

8. The dual-opening sample container, as described in claim 1, further comprising additional first and second securing caps, at least one of said additional caps further comprising a septa, said septa permitting introduction of a syringe needle and subsequent resealing of said securing cap.

9. The dual-opening sample container, as described in claim 1, wherein said first and second end seals comprise a substantially rigid core, said core being surrounded by a resilient material.

10. The dual-opening sample container, as described in claim 9, wherein said substantially rigid core and said resilient material are coated with substantially chemically inert material.

11. The dual-opening sample container, as described in claim 10, wherein said substantially chemically inert material is selected from the group comprising:
tetrafluoroethene, polytetrafluoroethene, perfluoralkoxy and fluoroethylpropylene.

12. The dual-opening sample container, as described in claim 1, wherein said first and second end seals further comprise a compressible seal, said seal permitting an elevation of fluid pressure within said sample container upon compression of said seal.

13. The dual-opening sample container, as described in claim 1, wherein at least one of said first and second end seals further comprises a resilient material, said resilient material permitting a elevation of fluid pressure within said sample container upon compression of said seal.

14. The dual-opening sample container, as described in claim 1, wherein said first and second end seals have a first side, said first side being substantially conical and being sized and shaped to fit sealably into said first and second open ends of said sample container.

15. The dual-opening sample container, as described in claim 1, wherein said first and second end seals have a second side, said second side having a substantially flat surface to mate with a flat inner side of either of said first and second securing caps.

16. The dual-opening sample container, as described in claim 1, wherein at least one of said first and second end seals have a membrane central portion, said central portion permitting introduction of a syringe needle through said end seals.

17. The dual-opening sample container, as described in claim 1, wherein said sample container is formed from material selected from the group comprising:
glass, steel and plastic.

18. The dual-opening sample container, as described in claim 1, wherein an outside diameter of said sample container ranges from 8 mm to 60 mm.

19. The dual-opening sample container, as described in claim 1, wherein an overall length of said sample container ranges from 20 mm to 150 mm.

20. The dual-opening sample container, as described in claim 1, wherein said sample container has a capacity ranging from 2 ml to 2400 ml.

21. A fluid sampling device with dual-opening sample containers, comprising:
at least one sample container, said container being formed of substantially rigid, fluid impermeable material and having a hollow cavity in communication with first and second open ends;
first and second end seals, said end seals being sized and shaped to fit sealably said first and second open ends;
a first elastic member, said first elastic member urging said first and second end seals to removably close said first and second open ends;
a support platform, said support platform being removably attached to said sample container and having a fixture for removable connection to a raising and lowering device;
said support platform having first and second movable attachment members, said attachment members being sized, shaped and disposed to removably engage said first and second end seals;
a trigger, said trigger disposed to move said attachment members from a first position to a second position;
further comprising a trigger sheath, said sheath being sized and shaped to fit slidably over said trigger and being attached at a first end to said support platform and extending upwardly about said trigger; and
whereby, when said sample container is attached to said support platform and said first and second end seals are engaged by said first and second attachment members in said first position, said sample container will be open, whereupon it may be lowered into a fluid source by said raising and lowering device and said trigger pulled to move said first and second attachment members to said second position releasing said first and second end seals, permitting said first elastic member to urge said first and second end seals to seal said first and second open ends of said sample container, thereby causing a fluid sample to be sealed within said sample container, said support platform may then be withdrawn from said fluid source with said sealed sample container and said fluid sample.

22. The fluid sampling device with dual-opening sample containers, as described in claim 21, further comprising a second elastic member, said second elastic member urging said attachment members to said first position.

23. The fluid sampling device with dual-opening sample containers, as described in claim 21, further comprising first and second activating protrusions, each of said activating protrusions extending outwardly from outer ends of said first and second end seals and being sized, shaped, and disposed to removably engage said movable attachment members.

24. The fluid sampling device with dual-opening sample containers, as described in claim 23, wherein said activating protrusion further comprises any of holes, loops and hooks for removable engagement of said movable attachment member.

25. The fluid sampling device with dual-opening sample containers, as described in claim 21, wherein said first and second end seals further comprise any of holes, loops and hooks for attachment to said first elastic member.

26. The fluid sampling device with dual-opening sample containers, as described in claim 21, wherein said first elastic member is disposed within said hollow cavity.

27. The fluid sampling device with dual-opening sample containers, as described in claim 21, wherein said first elastic member is disposed outside of said sample container.

28. The fluid sampling device with dual-opening sample containers, as described in claim 21, wherein said support platform has a hollow body, said hollow body being sized and shaped to enclose said sample container.

29. The fluid sampling device with dual-opening sample containers, as described in claim 28, wherein said support platform further comprises at least one fluid-permeable protective end cover, said end cover partially enclosing an open end of said hollow body.

30. The fluid sampling device with dual-opening sample containers, as described in claim 29, wherein said fixture for removable connection to a raising and lowering device is attached to said end cover.

31. The fluid sampling device with dual-opening sample containers, as described in claim 21, wherein said sampling container is sized and shaped to substantially enclose said support platform within outer horizontal dimensions of said sample container.

32. The fluid sampling device with dual-opening sample containers, as described in claim 21, wherein said first and second end seals comprise a substantially rigid core, said core being surrounded by a resilient material.

33. The fluid sampling device with dual-opening sample containers, as described in claim 32, wherein said substantially rigid core and said resilient material are coated with substantially chemically inert material.

34. The fluid sampling device with dual-opening sample containers, as described in claim 33, wherein said substantially chemically inert material is selected from the group comprising:
tetrafluoroethene, polytetrafluoroethene, perfluoralkoxy and fluoroethylpropylene.

35. The fluid sampling device with dual-opening sample containers, as described in claim 21, wherein said first and second end seals further comprise a compressible seal, said seal permitting an elevation of fluid pressure within said sample container upon compression of said seal.

36. The fluid sampling device with dual-opening sample containers, as described in claim 21, wherein at least one of said first and second end seals is formed of resilient material, said resilient material permitting an elevation of fluid pressure within said sample container upon compression of said seal.

37. The fluid sampling device with dual-opening sample containers, as described in claim 21, wherein said first and second end seals have a first side, said first side being substantially conical and being sized and shaped to fit sealably into said first and second open ends of said sample container.

38. The fluid sampling device with dual-opening sample containers, as described in claim 21, wherein at least one of said first and second end seals have a membrane central portion, said central portion permitting introduction of a syringe needle through said end seals.

39. The fluid sampling device with dual-opening sample containers, as described in claim 21, wherein said sample container is formed from material selected from the group comprising:
glass, steel and plastic.

40. The fluid sampling device with dual-opening sample containers, as described in claim 21, wherein an outside diameter of said sample container ranges from 8 mm to 60 mm.

41. The fluid sampling device with dual-opening sample containers, as described in claim 21, wherein an overall length of said sample container ranges from 20 mm to 150 mm.

42. The fluid sampling device with dual-opening sample containers, as described in claim 21, wherein said sample container has a capacity ranging from 2 ml to 2400 ml.

43. A fluid sampling device with dual-opening sample containers, comprising:

at least one sample container, said container being formed of substantially rigid, fluid impermeable material and having a hollow cavity in communication with first and second open ends;

first and second end seals, said end seals being sized and shaped to fit sealably said first and second open ends;

a first elastic member, said first elastic member urging said first and second end seals to removably close said first and second open ends;

a support platform, said support platform being removably attached to said sample container and having a fixture for removable connection to a raising and lowering device;

said support platform having first and second movable attachment members, said attachment members being sized, shaped and disposed to removably engage said first and second end seals;

a trigger, said trigger disposed to move said attachment members from a first position to a second position;

further comprising first and second securing caps, said securing caps being sized and shaped to retain said first and second end seals in sealable connection with said first and second open ends of said sampling container, wherein at least one of said first and second securing caps further comprises a septa permitting introduction of a syringe needle and subsequent resealing of said securing cap; and whereby, when said sample container is attached to said support platform and said first and second end seals are engaged by said first and second attachment members in said first position, said sample container will be open, whereupon it may be lowered into a fluid source by said raising and lowering device and said trigger pulled to move said first and second attachment members to said second position releasing said first and second end seals, permitting said first elastic member to urge said first and second end seals to seal said first and second open ends of said sample container, thereby causing a fluid sample to be sealed within said sample container, said support platform may then be withdrawn from said fluid source with said sealed sample container and said fluid sample.

44. The fluid sampling device with dual-opening sample containers, as described in claim 43, wherein said first and second open ends of said sampling container have an external thread and said first and second securing caps have a mating, internal thread.

45. The fluid sampling device with dual-opening sample containers, as described in claim 43, wherein said first and second open ends of said sampling container have an external bayonet mount and said first and second securing caps have a mating, internal bayonet mount.

46. The fluid sampling device with dual-opening sample containers, as described in claim 43, wherein said first and second end seals have a second side, said second side having a substantially flat surface to mate with a flat inner side of either of said first and second securing caps.

47. A method of sampling fluid using a fluid sampling device with dual-opening sample containers, comprising the steps of:

providing at least one sample container, said container being formed of substantially rigid, fluid impermeable material and having a hollow cavity in communication with first and second open ends;

providing first and second end seals, said end seals being sized and shaped to fit sealably said first and second open ends;

providing a first elastic member, said first elastic member urging said first and second end seals to removably close said first and second open ends;
providing a support platform, said support platform being removably attached to said sample container and having a fixture for removable connection to a raising and lowering device;
said support platform having first and second movable attachment members, said attachment members being sized, shaped and disposed to removably engage said first and second end seals;
providing a trigger, said trigger disposed to move said attachment members from a first position to a second position;
attaching said support platform to said sample container with said movable attachment members in said first position, engaging said first and second end seals to as to maintain said end seals in an open position;
attaching said support platform to said raising and lowering device;
lowering said support platform into a fluid source;
pulling said trigger to move said attachment members from said first position to said second position, thereby sealing said first and second open ends with a fluid sample inside of said hollow cavity;
raising said support platform from said fluid source;
removing said sealed sample container from said support platform; and
further comprising the steps of:
providing at least one of said first and second end seals with a membrane central portion, said central portion permitting introduction of a syringe needle through said end seal;
providing first and second securing caps, said securing caps being sized and shaped to retain said first and second end seals in sealable connection with said first and second open ends of said sampling container;
at least one of said securing caps having a septa permitting introduction of a syringe needle and subsequent resealing of said securing cap;
inserting a syringe needle through said septa and said membrane central portion;
withdrawing a fluid sample from said sample container;
removing said syringe needle from said septa and said membrane central portion; and
depositing said fluid sample in a test facility,
whereby, when said sample container is removed from said support platform, it may be sent for testing and examination without contamination from elements outside said fluid source.

48. The method of sampling fluid using a fluid sampling device with dual-opening sample containers, as described in claim 47, further comprising the steps of:
providing first and second securing caps, said securing caps being sized and shaped to retain said first and second end seals in sealable connection with said first and second open ends of said sampling container; and
attaching said first and second securing caps to said first and second open ends of said of said sample container.

49. A fluid sampling device with dual-opening sample containers, comprising:
at least one sample container, said container being formed of substantially rigid, fluid impermeable material and having a hollow cavity in communication with first and second open ends;
first and second end seals, said end seals being sized and shaped to fit sealably said first and second open ends;
a first elastic member, said first elastic member urging said first and second end seals to removably close said first and second open ends;
first and second activating protrusions, each of said activating protrusions extending outwardly from outer ends of said first and second end seals and being sized, shaped, and disposed to removably engage said movable attachment members;
first and second removable securing caps, said securing caps permitting passage of said activating protrusions through said securing caps and being sized and shaped to retain said first and second end seals in sealable connection with said first and second open ends of said sample container;
a support platform, said support platform being removably attached to said sample container and having a fixture for removable connection to a raising and lowering device;
said support platform having first and second movable attachment members, said attachment members being sized, shaped and disposed to removably engage said first and second end seals;
a trigger, said trigger disposed to move said attachment members from a first position to a second position; and
whereby, when said sample container is attached to said support platform and said first and second end seals are engaged by said first and second attachment members in said first position, said sample container will be open, whereupon it may be lowered into a fluid source by said raising and lowering device and said trigger pulled to move said first and second attachment members to said second position releasing said first and second end seals, permitting said first elastic member to urge said first and second end seals to seal said first and second open ends of said sample container, thereby causing a fluid sample to be sealed within said sample container, said support platform may then be withdrawn from said fluid source with said sealed sample container and said fluid sample.

50. The fluid sampling device with dual-opening sample containers, as described in claim 49, further comprising a trigger sheath, said sheath being sized and shaped to fit slidably over said trigger and being attached at a first end to said support platform and extending upwardly about said trigger.

51. The fluid sampling device with dual-opening sample containers, as described in claim 49, further comprising a second elastic member, said second elastic member urging said attachment members to said first position.

52. The fluid sampling device with dual-opening sample containers, as described in claim 49, wherein said activating protrusion further comprises any of holes, loops and hooks for removable engagement of said movable attachment member.

53. The fluid sampling device with dual-opening sample containers, as described in claim 49, wherein said first and second end seals further comprise any of holes, loops and hooks for attachment to said first elastic member.

54. The fluid sampling device with dual-opening sample containers, as described in claim 49, wherein said first elastic member is disposed within said hollow cavity.

55. The fluid sampling device with dual-opening sample containers, as described in claim 49, wherein said first elastic member is disposed outside of said sample container.

56. The fluid sampling device with dual-opening sample containers, as described in claim 49, wherein said first and second open ends of said sampling container have an external thread and said first and second securing caps have a mating, internal thread.

57. The fluid sampling device with dual-opening sample containers, as described in claim 49, wherein said first and second open ends of said sampling container have an external bayonet mount and said first and second securing caps have a mating, internal bayonet mount.

58. The fluid sampling device with dual-opening sample containers, as described in claim 49, wherein at least one of said first and second securing caps further comprises a septa permitting introduction of a syringe needle and subsequent resealing of said securing cap.

59. The fluid sampling device with dual-opening sample containers, as described in claim 49, wherein said support platform has a hollow body, said hollow body being sized and shaped to enclose said sample container.

60. The fluid sampling device with dual-opening sample containers, as described in claim 59, wherein said support platform further comprises at least one fluid-permeable protective end cover, said end cover partially enclosing an open end of said hollow body.

61. The fluid sampling device with dual-opening sample containers, as described in claim 60, wherein said fixture for removable connection to a raising and lowering device is attached to said end cover.

62. The fluid sampling device with dual-opening sample containers, as described in claim 49, wherein said sampling container is sized and shaped to substantially enclose said support platform within outer horizontal dimensions of said sample container.

63. The fluid sampling device with dual-opening sample containers, as described in claim 49, wherein said first and second end seals comprise a substantially rigid core, said core being surrounded by a resilient material.

64. The fluid sampling device with dual-opening sample containers, as described in claim 63, wherein said substantially rigid core and said resilient material are coated with substantially chemically inert material.

65. The fluid sampling device with dual-opening sample containers, as described in claim 64, wherein said substantially chemically inert material is selected from the group comprising:
tetrafluoroethene, polytetrafluoroethene, perfluoralkoxy and fluoroethylpropylene.

66. The fluid sampling device with dual-opening sample containers, as described in claim 49, wherein said first and second end seals further comprise a compressible seal, said seal permitting an elevation of fluid pressure within said sample container upon compression of said seal.

67. The fluid sampling device with dual-opening sample containers, as described in claim 49, wherein at least one of said first and second end seals is formed of resilient material, said resilient material permitting an elevation of fluid pressure within said sample container upon compression of said seal.

68. The fluid sampling device with dual-opening sample containers, as described in claim 49, wherein said first and second end seals have a first side, said first side being substantially conical and being sized and shaped to fit sealably into said first and second open ends of said sample container.

69. The fluid sampling device with dual-opening sample containers, as described in claim 49, wherein said first and second end seals have a second side, said second side having a substantially flat surface to mate with a flat inner side of either of said first and second securing caps.

70. The fluid sampling device with dual-opening sample containers, as described in claim 49, wherein at least one of said first and second end seals have a membrane central portion, said central portion permitting introduction of a syringe needle through said end seals.

71. The fluid sampling device with dual-opening sample containers, as described in claim 49, wherein said sample container is formed from material selected from the group comprising:
glass, steel and plastic.

72. The fluid sampling device with dual-opening sample containers, as described in claim 49, wherein an outside diameter of said sample container ranges from 8 mm to 60 mm.

73. The fluid sampling device with dual-opening sample containers, as described in claim 49, wherein an overall length of said sample container ranges from 20 mm to 150 mm.

74. The fluid sampling device with dual-opening sample containers, as described in claim 49, wherein said sample container has a capacity ranging from 2 ml to 2400 ml.

75. A method of sampling fluid using a fluid sampling device with dual-opening sample containers, comprising the steps of:
providing at least one sample container, said container being formed of substantially rigid, fluid impermeable material and having a hollow cavity in communication with first and second open ends;
providing first and second end seals, said end seals being sized and shaped to fit sealably said first and second open ends;
providing a first elastic member, said first elastic member urging said first and second end seals to removably close said first and second open ends;
providing first and second activating protrusions, each of said activating protrusions extending outwardly from outer ends of said first and second end seals and being sized, shaped, and disposed to removably engage said movable attachment members;
providing first and second removable securing caps, said securing caps permitting passage of said activating protrusions through said securing caps and being sized and shaped to retain said first and second end seals in sealable connection with said first and second open ends of said sample container;
providing a support platform, said support platform being removably attached to said sample container and having a fixture for removable connection to a raising and lowering device;
said support platform having first and second movable attachment members, said attachment members being sized, shaped and disposed to removably engage said first and second end seals;
providing a trigger, said trigger disposed to move said attachment members from a first position to a second position;
attaching said support platform to said sample container with said movable attachment members in said first position, engaging said first and second end seals to as to maintain said end seals in an open position;
attaching said support platform to said raising and lowering device;
lowering said support platform into a fluid source;
pulling said trigger to move said attachment members from said first position to said second position, thereby sealing said first and second open ends with a fluid sample inside of said hollow cavity;

raising said support platform from said fluid source;
removing said sealed sample container from said support platform; and
whereby, when said sample container is removed from said support platform, it may be sent for testing and examination without contamination from elements outside said fluid source.

76. The method of sampling fluid using a fluid sampling device with dual-opening sample containers, as described in claim 75, further comprising the step of attaching said first and second securing caps to said first and second open ends of said of said sample container.

77. The method of sampling fluid using a fluid sampling device with dual-opening sample containers, as described in claim 75, further comprising the steps of:
providing at least one of said first and second end seals with a membrane central portion, said central portion permitting introduction of a syringe needle through said end seal;
at least one of said securing caps having a septa permitting introduction of a syringe needle and subsequent resealing of said securing cap;
inserting a syringe needle through said septa and said membrane central portion;
withdrawing a fluid sample from said sample container;
removing said syringe needle from said septa and said membrane central portion; and
depositing said fluid sample in a test facility.

78. A dual-opening sample container, comprising:
a body, said body being formed of substantially rigid, fluid impermeable material and having a hollow cavity in communication with first and second open ends;
first and second end seals, said end seals being sized and shaped to fit sealably said first and second open ends;
at least one of said first and second end seals having a solid membrane central portion with one side that partially defines the cavity and another side that is exposed to the ambient when in a closed position, said central portion permitting introduction of a syringe needle through the longitudinal axis of said end seal;
a first elastic member, said first elastic member urging said first and second end seals to removably close said first and second open ends;
first and second activating protrusions, each of said activating protrusions extending outwardly from outer ends of said first and second end seals and being sized, shaped, and disposed to removably engage means for holding open said end seals.

79. The dual-opening sample container, as described in claim 78, further comprising first and second securing caps, at least one of said caps further comprising a septa, said septa permitting introduction of a syringe needle and subsequent resealing of said securing cap.

80. A fluid sampling device with dual-opening sample container, comprising:
at least one sample container, said container being formed of substantially rigid, fluid impermeable material and having a hollow cavity in communication with first and second open ends;
first and second end seals, said end seals being sized and shaped to fit sealably said first and second open ends;
at least one of said first and second end seals having a solid membrane central portion with one side that partially defines the cavity and another side that is exposed to the ambient when in a closed position, said central portion permitting introduction of a syringe needle through the longitudinal axis of said end seal;
a first elastic member, said first elastic member urging said first and second end seals to removably close said first and second open ends;
first and second activating protrusions, each of said activating protrusions extending outwardly from outer ends of said first and second end seals and being sized, shaped, and disposed to removably engage said movable attachment members;
a support platform, said support platform being removably attached to said sample container and having a fixture for removable connection to a raising and lowering device;
said support platform having first and second movable attachment members, said attachment members being sized, shaped and disposed to removably engage said first and second end seals;
a trigger, said trigger disposed to move said attachment members from a first position to a second position; and
whereby, when said sample container is attached to said support platform and said first and second end seals are engaged by said first and second attachment members in said first position, said sample container will be open, whereupon it may be lowered into a fluid source by said raising and lowering device and said trigger pulled to move said first and second attachment members to said second position releasing said first and second end seals, permitting said first elastic member to urge said first and second end seals to seal said first and second open ends of said sample container, thereby causing a fluid sample to be sealed within said sample container, said support platform may then be withdrawn from said fluid source with said sealed sample container and said fluid sample.

81. The fluid sampling device with dual-opening sample container, as described in claim 80, further comprising first and second securing caps, at least one of said caps further comprising a septa, said septa permitting introduction of a syringe needle and subsequent resealing of said securing cap.

* * * * *